United States Patent [19]
Macaulay et al.

[11] Patent Number: 5,234,416
[45] Date of Patent: Aug. 10, 1993

[54] INTRAVASCULAR CATHETER WITH A NONTRAUMATIC DISTAL TIP

[75] Inventors: Patrick E. Macaulay, Cupertino; Lawrence D. Wasicek, Sunnyvale; Alfredo Bayot, Newark; Kurt Klemm, Santa Clara, all of Calif.

[73] Assignee: Advanced Cardiovascular Systems, Inc., Santa Clara, Calif.

[21] Appl. No.: 711,045

[22] Filed: Jun. 6, 1991

[51] Int. Cl.⁵ ............................................. A61M 25/00
[52] U.S. Cl. .................................. 604/282; 604/264; 128/658
[58] Field of Search ................. 604/96, 264, 280, 282; 128/656–658, 772; 138/120, 123–126

[56] References Cited

U.S. PATENT DOCUMENTS

| | | | |
|---|---|---|---|
| 4,425,919 | 1/1984 | Alston, Jr. et al. | 128/658 |
| 4,636,346 | 1/1987 | Gold et al. | 604/280 X |
| 4,690,175 | 9/1987 | Ouchi et al. | 138/131 |
| 4,863,442 | 9/1989 | DeMello et al. | 604/282 |
| 4,898,591 | 2/1990 | Jang et al. | 604/282 |
| 5,037,407 | 8/1991 | Gold et al. | 604/282 |
| 5,045,072 | 9/1991 | Castillo et al. | 604/280 |

FOREIGN PATENT DOCUMENTS

| | | |
|---|---|---|
| 0303487 | 2/1989 | European Pat. Off. . |
| 0334640 | 9/1989 | European Pat. Off. . |
| 0453008 | 10/1991 | European Pat. Off. . |
| 92108883 | 4/1992 | European Pat. Off. . |
| 2140755 | 2/1973 | Fed. Rep. of Germany . |
| 2954391 | 10/1985 | Fed. Rep. of Germany . |

*Primary Examiner*—C. Fred Rosenbaum
*Assistant Examiner*—C. Maglione

[57] ABSTRACT

An intravascular catheter such as a guiding catheter of composite construction having a nontraumatic distal tip comprising a proximal elastomeric tubular element and a distal elastomeric tubular element formed of softer material that the proximal section. The proximal tubular section of the distal tip preferably has a radiopaque material incorporated therein to enable the distal tip to be fluoroscopically observable when in place within a patient. The shaft of the catheter, which exhibits excellent torquability and pushability, is formed with a very thin wall. The catheter shaft includes an inner tubular member of braided polymeric fibrous strands impregnated with a thermoset polyurethane and having an outer jacket or coating of thermoplastic polyurethane secured to the braided tubular member. In some embodiments it is preferred to include a lubricous liner within the braided tubular member.

19 Claims, 1 Drawing Sheet

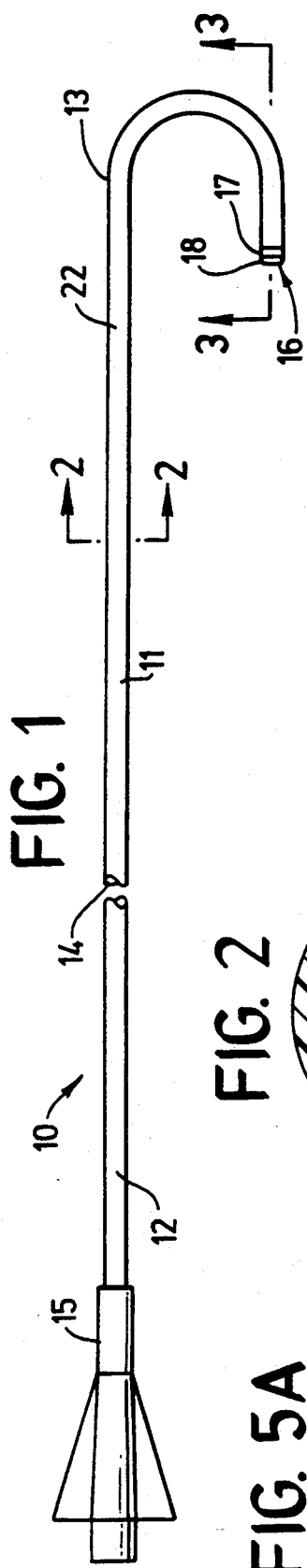
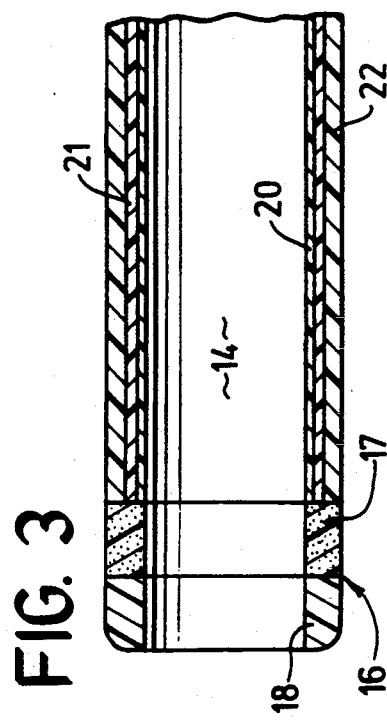
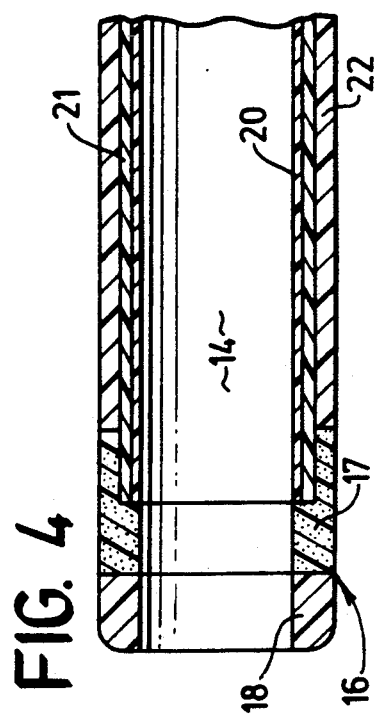
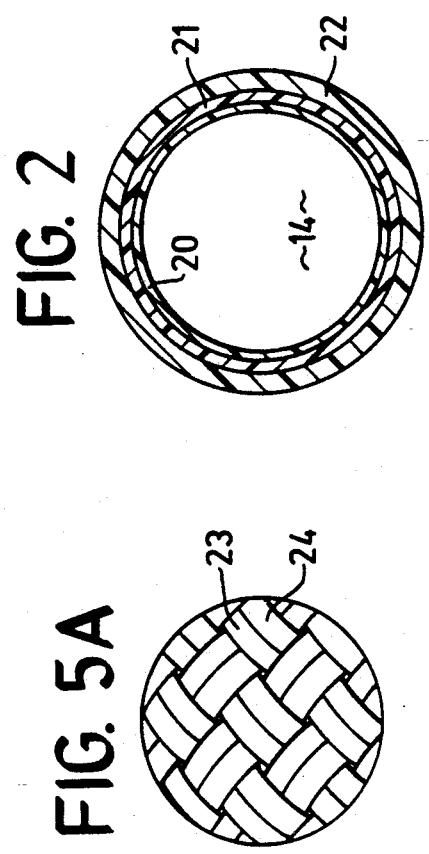
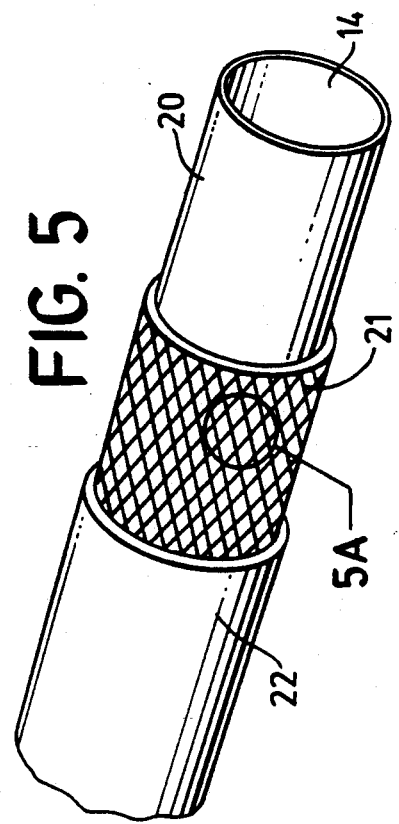

INTRAVASCULAR CATHETER WITH A NONTRAUMATIC DISTAL TIP

BACKGROUND OF THE INVENTION

This invention generally relates to guiding catheters for use in intravascular procedures such as percutaneous transluminal coronary angioplasty (PTCA).

In classic PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from its proximal end which extends out of the patient to turn the distal tip of the guiding catheter so that it can be guided into the coronary ostium. A guidewire and a dilatation catheter having a balloon on the distal end thereof are introduced into and advanced through the guiding catheter to the distal tip thereof, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. The balloon is then deflated so that the dilatation catheter can be removed from the dilated stenosis and blood flow resumed therethrough.

Further details of guiding catheters, dilatation catheters, guidewires, and the like used in angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); and U.S. Pat. No. 4,898,577 (Badger et al.) which are hereby incorporated herein in their entirety by reference thereto.

Guiding catheters are frequently provided with soft distal tips in order minimize trauma to the arterial lining as the guiding catheter is advanced through an arterial passageway. See for example U.S. Pat. No. 4,385,635 (Ruiz) which is incorporated herein by reference. Soft distal tips may reduce arterial trauma, but they do not always provide a smooth transition between the distal tip and the catheter shaft proximal thereto. Additionally, the soft distal tips are very difficult to locate fluoroscopically by the physician when guiding the distal tip into the ostium of the desired coronary artery.

What has been needed and heretofore unavailable is a guiding catheter or other similar catheter with a nontraumatic distal tip which provides a smooth transition with the catheter shaft and is fluoroscopically observable by the physician in order to facilitate the advancement thereof through a patient's vasculature. The present invention satisfies that need.

SUMMARY OF THE INVENTION

The present invention is directed to a guiding catheter, and particularly to a guiding catheter with a nontraumatic distal tip.

The catheter of the invention generally includes an elongated, tubular shaft having proximal and distal ends, an inner lumen extending therein and a flexible nontraumatic distal tip which is significantly softer than the catheter shaft to which it is secured. The nontraumatic distal tip has at least two, relatively short elastomeric or rubber-like tubular elements which are coaxially secured to the distal end of the tubular shaft. The soft tip is designed with progressively stiffer elements in the proximal direction toward the tubular shaft so that when the tip contacts a blood vessel wall, the force thereof is transmitted to the tubular shaft in a transitionless manner, causing it to align with the flow-line of the vessel. The most distal of the elastomeric tubular elements is softer and more pliable than the elastomeric tubular element proximally adjacent thereto and should have a durometer hardness of at least a Shore 10 A hardness less than the adjacent proximal tubular element. The proximal tubular element should have a durometer hardness of about a Shore 80 A to about a Shore 100 A and the distal tubular element should have a durometer hardness of about a Shore 70 A to about a Shore 90 A. The proximal elastomeric tubular element is formed with radiopaque material incorporated therein to facilitate the fluoroscopic observation thereof when disposed within a patient's body lumen such as an artery.

The tubular shaft of the catheter is preferably of composite construction with an elongated braided tubular member formed from radially compressive multifilament polymeric strands, which is impregnated with a thermoset polymer and provided with an outer jacket of thermoplastic polymer. An inner lubricous liner formed of suitable lubricous material such as fluorinated ethylene propylene or polytetrafluoroethylene (e.g., Teflon®, a registered trademark of E. I. du Pont, de Nemours & Co., Inc.) may be provided on the interior of the braided tubular member to thereby define the inner lumen extending within the catheter shaft.

To provide greater flexibility in the distal section of the catheter shaft, the distal section of the braided tubular member may be impregnated with a softer thermoset polymer than the thermoset polymer which impregnates the proximal section of the tubular braided member.

In one preferred embodiment the catheter of the invention is a highly torquable guiding catheter which is readily advanced within a patient's vascular system and, when torqued from the proximal end, it has little tendency to store energy along the length thereof and to release the stored energy by the sudden rotation of the distal end of the catheter, i.e. does not cause the distal end of the catheter to whip. Moreover, the composite structure of the catheter ensures that the circularity of the inner lumen thereof is maintained, so there is little likelihood that a guidewire or dilatation catheter will become bound-up within the lumen when the catheter passes through tortuous passageways. The elastomeric tubular elements forming the nontraumatic distal tip of the catheter are intended to minimize the risk of traumatic engagements with arterial linings and allows the distal tip to be fluoroscopically observable.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view of a guiding catheter embodying features of the invention.

FIG. 2 is a transverse cross-sectional view of the catheter shown in FIG. 1 taken along the lines 2—2.

FIG. 3 is an enlarged longitudinal centerline cross-sectional view of the distal tip of the catheter shown in FIG. 1 taken along the lines 3—3.

FIG. 4 is an enlarged longitudinal centerline cross-sectional view of an alternate construction of the distal tip of a catheter embodying features of the invention.

FIG. 5 is a perspective view of the shaft of the catheter shown in FIG. 1 with sections exposed.

FIG. 5A is an expanded view of the braided section circled in FIG. 5.

DETAILED DESCRIPTION OF THE INVENTION

FIGS. 1–5 and 5A schematically illustrate a guiding catheter 10 of the invention which generally includes an elongated catheter shaft 11 having a proximal section 12, a more flexible distal section 13, an inner lumen 14 extending therein, a Luer hub 15 on the proximal end of the shaft and a nontraumatic distal tip 16 comprising two relatively short elastomeric tubular elements 17 and 18 which are coaxially disposed. The distal section 13 of the shaft 11 is shaped to facilitate the entry thereof into the ostium of a desired coronary artery. As will be appreciated by those skilled in the art, the J-shape of the distal section 13 of the catheter shown in FIG. 1 is a schematic representation and a variety of shapes, such as the well-known Judkins and Amplatz configurations for both the right and left coronary arteries, may be employed to facilitate the entry of the distal tip of the guiding catheter into the ostium of the desired coronary artery. The relatively soft, nontraumatic distal tip 16 is intended to minimize traumatic engagement with arterial tissue.

FIGS. 2, 5 and 5A illustrate the composite construction of the shaft 11 of catheter 10. A thin-walled lubricous inner lining 20 is disposed within braided tubular element 21 and defines the inner lumen 14. The braided tubular element 21 is impregnated with a thermoset polymeric material and an outer jacket 22, preferably formed of a thermoplastic polymeric material, surrounds the exterior of the braided tubular element 21. The braided tubular element 21 is formed from a plurality of pairs of fibrous multifilament polymeric strands 23 and 24 which are radially compressed against the inner liner 20 when they are braided into the diamond-like pattern as shown in FIG. 5A.

The nontraumatic distal tip 16 of the catheter 10, as illustrated in FIG. 3, is comprised of two relatively short flexible tubular elements, a proximal element 17 and a distal element 18, and is butt joined to the distal end of shaft 11 by melt fusing or by a suitable adhesive, such as well-known cyanoacrylate-based adhesives, e.g. Loctite TM 405, sold by Loctite Corporation, Newington, Conn. Both tubular elements 17 and 18 are formed of elastomeric or rubber-like materials but the distal section 18 is softer and more flexible than proximal section 17. Additionally, the proximal section 17 has a radiopaque filler material incorporated therein such as bismuth trioxide in order to make the distal tip fluoroscopically observable within a patient. The short tubular sections 17 and 18 are also butt joined together by suitable means such as by heat fusing or by a suitable adhesive such as a cyanoacrylate-based adhesive, e.g. Loctite TM 405.

FIG. 4 illustrates a presently preferred construction for the nontraumatic distal tip 16 wherein the proximal tubular element 17 has a stepped construction which extends over a shoulder provided at the distal end of the shaft 11. Otherwise, the distal tip is the same as described above for the embodiment shown in FIG. 3.

In one presently preferred embodiment of the invention, the inner lubricous lining 20 has a wall thickness of about 0.002 inch (0.051 mm), the braided tubular member 21 and the thermoset polymer matrix into which it is disposed has a wall thickness of about 0.003 inch (0.076 mm) and the outer jacket 22 has a wall thickness of about 0.005 inch (0.13 mm). The diameter of the inner lumen 14 extending within the inner lining 20 may range from about 0.06 to about 0.09 inch (1.5–2.3 mm). The overall length of the catheter 10 for coronary angioplasty may range from about 80 to about 125 cm.

The catheter shaft 11 is preferably manufactured by braiding a plurality of pairs of fibrous strands 23 and 24 onto the tubular inner liner 20 or, in the alternative, a mandrel (not shown) and then impregnating the fibrous braid with a thermoset polymeric material to form a tubular element 21. The distal section 13, which may be the most distal 5 to 20 cm of the shaft 11, may be impregnated with a thermoset polymer which cures to a softer material than that impregnating the proximal section 12 to provide a greater degree of flexibility to the distal section 13. In a presently preferred method of forming the product, a thermoplastic tubular member or sleeve which forms the outer jacket 22 is fit onto the impregnated, braided tubular element 21, and then a heat shrinkable tubular element (not shown) is fit over the thermoplastic tube forming the outer jacket 22 and the assembly is then heated to shrink the heat shrinkable tube and press the thermoplastic jacket 22 against the exterior of the braided tubular element 21 to secure the jacket thereto. Upon cooling, the heat shrinkable tube is slit along its length and then peeled off the jacket 22.

The relatively short tubular elements 17 and 18 and the tip are butt joined together by suitable means such as fusion bonding to the distal end of the shaft 11. Luer hub 15 may be secured to the proximal end of the shaft 11. The distal section 13 of the catheter shaft 11 may be shaped to the desired configuration for its intended end use when the thermoset impregnate is cured or it may be heated and shaped after the catheter 10 has been made, for example, by the physician before the catheter is inserted into the patient.

One presently preferred thermoset polymer for impregnating the proximal section of the braided tubular element 21 is a polyurethane, such as two component polyurethane RP 6414-3 (resin and hardener) sold by the Ciba-Geigy Corporation and the presently preferred thermoset polymer for impregnating the distal end portion of the braided tubular element is also a polyurethane, such as two component polyurethane RP 6413-1 (resin and hardener) also sold by the same company. The resin/hardener ratios (by weight) for these polyurethane polymers are typically about 100/60. These polymers will cure at about 200 degrees F. or at room temperature. Preferably, the polymers are partially cured at an elevated temperature (e.g. 200 degrees F.) and then are allowed to completely cure at room temperature. Other polymer systems such as epoxy based systems may also be used.

The thermoplastic jacket or coating 22 is preferably formed of a thermoplastic polyurethane made with a polytetramethylene glycol ether such 2363 55DE Pellethane which is available from the Dow Chemical Company or a polyurethane such as Texin-965 DM which is available from the Mobay Corporation.

The cured properties for the above polymers (7 days @ 77° F.) are set forth in the following table.

| PROPERTY TESTED | METHOD OF TESTING (ASTM) | 6413 | 6414 | PELLETANE 2363-55DE |
| --- | --- | --- | --- | --- |
| DENSITY | D-792 | 1.06 | 1.08 | 1.15 |
| HARDNESS | D-2224D | 90-95A | 55-65D | 55D |
| TENSILE STRENGTH | D-638 (D-412) | 2500 psi | 2500 psi | 6500 psi |
| ULTIMATE ELONGATION | D-638 (D-412) | 400% | 250% | 450% |
| TEAR STRENGTH | D-624 | 350 psi | 550 psi | 600 psi |
| COMP SET | D-395 | 68% | 89% | 75% |
| TABER WEAR | D-1044 (C-501) | 4.0 mg | 8.6 mg | 70(H-22) |

The relatively short tubular elements 17 and 18 of the non-traumatic distal tip 16 of the catheter are preferably formed from aliphatic polyurethanes which are available from Thermedics Inc. of Woburn, Mass. under the trade name Tecoflex. A radiopaque grade of the Tecoflex resin, EG93A-HT60, is preferably used for the proximal section 17 and a softer nonradiopaque grade, EG80A, is preferably used for the distal section 18. Other grades of polyurethane, other elastomer systems and rubber-like materials may be employed.

The dimensions of the proximal and distal tubular sections of the non-traumatic distal tip varies depending upon the dimensions of the catheter. Generally, the length of the tubular sections 17 and 18 is less than the outside diameter thereof. For most guiding catheters the length of the proximal radiopaque section 17 will be about 1 to about 10 mm, typically about 2 to about 2.5 mm, and the length of the distal section will be about 0.5 to about 4 mm, typically about 0.5 to about 1 mm. The outside diameters of both sections range from about 0.09 to about 0.15 inch (2.3-3.7 mm), typically about 0.1 inch (2.54 mm), and the inside diameters thereof range from about 0.07 to about 0.09 inch (1.78-2.3 mm), typically about 0.08 inch (2.0 mm). Greater or lesser dimensions may be used depending upon the particular end use of the catheter.

The multifilament polymeric fibrous strands employed to form the braided tubular element are preferably about 50 to about 200 denier and may be formed from a fibrous polymeric material such as aramid (e.g. Kevlar 49 sold by du Pont) and a polyester (e.g. Vectran). Other polymeric materials may be suitable. A 2×2 braid pattern shown in FIG. 5A is preferred and may be formed using 16 carriers with one bobbin per carrier. To facilitate the bonding of the polymer matrix which is incorporated into the braided tubular element 21 to a liner 20 formed of fluorinated ethylene propylene, the outer surface of the lining is etched with sodium naphthalene. In lieu of impregnating the braided tubular element after its formation with a thermoset plastic, in some instances it may be convenient to intermix thermoplastic fibers, such as polyester fibers, as adhesive with the multifilament fibers so that the tubular element is braided with the thermoset fibers incorporated therein. Heating of the braided tubular element will cure the incorporated polyester.

While the invention has been primarily described herein in terms of a guiding catheter with two relatively soft tubular elements forming the nontraumatic distal tip, it will be apparent to those skilled in the art that the distal tip may be formed from three or more of these relatively soft tubular elements with the durometer hardnesses thereof increasing in each element from the most distal element to the most proximal element. Moreover, the invention can be employed in a variety of intravascular catheters other than guiding catheters, such as peripheral guides and angiographic guides, other modifications and improvements can be made to the invention without departing from the scope thereof.

What is claimed is:

1. An intravascular catheter comprising:
   a) a tubular shaft having proximal and distal ends with an inner lumen extending therein and comprising:
      a braided tubular member formed of a plurality of multifilament strands which are impregnated with a thermoset polymeric resin, the thermoset polymer resin which is incorporated into a distal portion of the braided tubular member having a cured hardness less than the cured hardness of the thermoset polymer resin which is incorporated into a proximal portion of the braided tubular member;
      a lubricous polymeric lining extending longitudinally through the braided tubular member and defining the inner lumen extending within the elongated shaft of the guiding catheter; and
      a thermoplastic polymeric jacket on the exterior of the braided tubular member;
   b) a relatively short and straight nontraumatic distal tip having at least two relatively short, coaxially disposed flexible tubular elements, including a first tubular element which is secured to the distal end of the catheter shaft, and a second tubular element which is secured to the first tubular element and which is softer than the first tubular element.

2. The intravascular catheter of claim 1 wherein the flexible tubular elements are formed of elastomeric or other rubber-like materials.

3. The intravascular catheter of claim 1 wherein the second tubular element has a durometer hardness of at least about Shore 10 A less than the Shore hardness of the first tubular element.

4. The intravascular catheter of claim 1 wherein the second tubular element has a durometer hardness of about Shore 70 A to about Shore 90 A.

5. The intravascular catheter of claim 1 wherein the first tubular element has a durometer hardness of about Shore 80 A to about Shore 100 A.

6. The intravascular catheter of claim 1 wherein the thermoset polymeric resin which is incorporated into the braided tubular member is a polyurethane.

7. The intravascular catheter of claim 1 wherein the thermoplastic polymeric jacket is a polyurethane.

8. The intravascular catheter of claim 1 wherein multifilament strands are formed of one or more materials selected from the group consisting of aramid and polyester.

9. The intravascular catheter of claim 1 wherein the braided tubular member has a double strand, diamond-shaped construction.

10. A torquable guiding catheter having an elongated tubular shaft with an inner lumen extending therein and having a preformed distal portion with a soft, relatively short and straight distal tip which facilitates a nontraumatic advancement through a patient's vasculature, comprising:
   a) an elongated tubular shaft having proximal and distal ends, an inner lumen extending therein and a preformed distal portion, the shaft comprising:
      a braided tubular member formed of a plurality of multifilament strands which are impregnated with a thermoset polymeric resin, the braided tubular member having a distal end which has impregnated with a thermoset polymer resin having a cured hardness less than the cured hardness of the thermoset polymer impregnating the braided tubular member proximal thereto,
      a thermoplastic polymeric jacket on the exterior of the braided tubular member, and
   b) a nontraumatic tip secured to the distal end of the elongated shaft comprising a relatively short elastomeric proximal tubular element and, in a coaxial configuration therewith, a relatively short elastomeric distal tubular element, with the distal tubular element being softer than the proximal tubular element.

11. The guiding catheter of claim 10 wherein the braided tubular member is formed of radially compressed multifilament polymeric strands impregnated with thermoset polymeric resin.

12. The guiding catheter of claim 10 wherein the thermoset polymeric resin which is incorporated into the braided multifilament polymeric strands is a polyurethane.

13. The guiding catheter of claim 10 wherein the thermoplastic polymeric jacket is a polyurethane.

14. The guiding catheter of claim 10 wherein the multifilament strands are formed of a material selected from the group consisting of aramid and polyester.

15. The guiding catheter of claim 10 wherein the multifilament polymeric strands are braided into a double strand, diamond shaped construction.

16. The guiding catheter of claim 10 including a lubricous polymeric lining extending longitudinally through the braided tubular member and defining the inner lumen extending within the elongated shaft of the guiding catheter.

17. The intravascular catheter of claim 10 wherein the distal tubular element has a durometer hardness of at least about Shore 10 A lower than the durometer hardness of the proximal tubular element.

18. The intravascular catheter of claim 10 wherein the distal tubular element has a durometer hardness of about Shore 70 A to about Shore 90 A.

19. The intravascular catheter of claim 10 wherein the proximal tubular element has a durometer hardness of about Shore 80 A to about Shore 100 A.

* * * * *